US010828263B2

(12) United States Patent
Edirisinghe et al.

(10) Patent No.: US 10,828,263 B2
(45) Date of Patent: Nov. 10, 2020

(54) LAYERED BODIES AND COMPOSITIONS CONTAINING THEM

(71) Applicant: UCL Business PLC, London (GB)

(72) Inventors: Mohan Edirisinghe, Uxbridge (GB);
Ming Wei Chang, Taiping (TW);
Eleanor Stride, London (GB)

(73) Assignee: UCL Business Ltd, London (GB)

( * ) Notice: Subject to any disclaimer, the term of this patent is extended or adjusted under 35 U.S.C. 154(b) by 0 days.

(21) Appl. No.: 15/833,452

(22) Filed: Dec. 6, 2017

(65) Prior Publication Data

US 2018/0092860 A1  Apr. 5, 2018

Related U.S. Application Data

(63) Continuation of application No. 13/984,345, filed as application No. PCT/GB2012/050276 on Feb. 8, 2012, now abandoned.

(30) Foreign Application Priority Data

Feb. 8, 2011 (GB) .................................. 1102148.2

(51) Int. Cl.
| | | |
|---|---|---|
| A61K 9/70 | (2006.01) | |
| B29C 48/21 | (2019.01) | |
| A61K 49/22 | (2006.01) | |
| B01J 13/22 | (2006.01) | |
| A61K 9/48 | (2006.01) | |

(52) U.S. Cl.
CPC .............. *A61K 9/70* (2013.01); *A61K 9/4808* (2013.01); *A61K 9/4816* (2013.01); *A61K 9/4891* (2013.01); *A61K 49/226* (2013.01); *B01J 13/22* (2013.01); *B29C 48/21* (2019.02); *Y10T 428/2933* (2015.01); *Y10T 428/2938* (2015.01)

(58) Field of Classification Search
CPC ...... A61K 9/70; A61K 9/4808; A61K 9/4816; A61K 9/4891; A61K 49/226; B29C 48/21; B01J 13/22
See application file for complete search history.

(56) References Cited

U.S. PATENT DOCUMENTS

| | | | |
|---|---|---|---|
| 3,429,827 A * | 2/1969 | Ruus ........................ | B01J 13/16 106/31.14 |
| 5,811,187 A | 9/1998 | Anderson et al. | |
| 6,063,365 A | 5/2000 | Shefer et al. | |
| 6,193,951 B1 * | 2/2001 | Ottoboni ............ | A61K 41/0028 424/9.5 |
| 6,491,902 B2 | 12/2002 | Shefer et al. | |
| 6,589,562 B1 | 7/2003 | Shefer et al. | |
| 6,669,961 B2 * | 12/2003 | Kim ..................... | A61K 9/1694 424/400 |
| 6,767,637 B2 | 7/2004 | Park et al. | |
| 6,805,904 B2 | 10/2004 | Anders et al. | |
| 6,825,161 B2 | 11/2004 | Shefer et al. | |
| 7,368,130 B2 * | 5/2008 | Kim ..................... | A61K 9/1694 424/489 |
| 7,544,770 B2 | 6/2009 | Haynie | |
| 7,736,582 B2 | 6/2010 | Toth | |
| 8,297,959 B2 * | 10/2012 | Larsen ................. | A61K 9/5094 264/13 |
| 8,404,275 B2 | 3/2013 | Habboushe | |
| 2001/0012522 A1 | 8/2001 | Ottoboni et al. | |
| 2003/0219384 A1 | 11/2003 | Donath et al. | |
| 2004/0052984 A1 | 3/2004 | Toth | |
| 2004/0086459 A1 * | 5/2004 | Ottoboni ............ | A61K 41/0028 424/9.52 |
| 2004/0161498 A1 | 8/2004 | Ripoll et al. | |
| 2005/0123614 A1 | 6/2005 | Kim et al. | |
| 2005/0163714 A1 | 7/2005 | Sukhishivili et al. | |
| 2005/0208100 A1 | 9/2005 | Weber et al. | |
| 2005/0275143 A1 | 12/2005 | Toth | |
| 2006/0099247 A1 | 5/2006 | Cantwell et al. | |
| 2007/0248661 A1 * | 10/2007 | Andra .................. | A61K 9/0009 424/452 |
| 2008/0050610 A1 | 2/2008 | Stumber et al. | |
| 2008/0181964 A1 | 7/2008 | Kim et al. | |
| 2008/0226741 A1 | 9/2008 | Richard | |
| 2009/0081130 A1 * | 3/2009 | Ottoboni ............ | A61K 41/0028 424/9.52 |
| 2009/0170693 A1 | 7/2009 | Ikeda | |
| 2010/0015224 A1 | 1/2010 | Singh et al. | |
| 2010/0166810 A1 | 7/2010 | Habboushe | |

FOREIGN PATENT DOCUMENTS

| | | | |
|---|---|---|---|
| EP | 1364718 B1 | 10/2007 | |
| WO | 9112823 A1 | 9/1991 | |
| WO | WO-9112823 A1 * | 9/1991 | ............. A61B 8/481 |
| WO | 2008119945 A2 | 10/2008 | |

OTHER PUBLICATIONS

Chang et al. Stimulus-responsive liquids for encapsulation storage and controlled release of drugs from from nano-shell capsules. J. R. Soc. Interface, online Oct. 13, 2010, 8(56): 451-456. (Year: 2010).*
Gratton et al. The effect of particle design on cellular internalization pathways. PNAS, 2008, 105(33): 11613-11618. (Year: 2008).*
Khopade et al. Ultrathin Antibiotic Walled Microcapsules. Biomacromolecules 2005, 6, 229-234. (Year: 2005).*
Ahmad et al., "Generation of multilayered structures for biomedical applications using a novel tri-needle coaxial device and electrohydrodynamic flow", Journal of The Royal Society Interface, 2008, vol. 5, pp. 1255-1261.

(Continued)

*Primary Examiner* — Robert A Wax
*Assistant Examiner* — Olga V. Tcherkasskaya
(74) *Attorney, Agent, or Firm* — Bookoff McAndrews, PLLC

(57) ABSTRACT

A layered body comprising: a core region; at least one intermediate layer disposed around the core region; and an outer layer disposed around the at least one intermediate layer, wherein at least one of the at least one intermediate layers comprises a gas, the layered body having at least one dimension, measured across the body and through the core region, of 100 μm or less.

16 Claims, 9 Drawing Sheets

(56) References Cited

OTHER PUBLICATIONS

Ahmad et al., "Engineering a material for biomedical applications with electric field assisted processing", Applied Physics A, 2009, vol. 97, pp. 31-37.
Chang et al., "Stimulus-responsive liquids for encapsulation storage and controlled release of drugs from nano-shell capsules", Journal of The Royal Society Interface, 2011, vol. 8, pp. 451-456.
Enayati et al., "Electrohydrodynamic preparation of particles, capsules and bubbles for biomedical engineering applications", Colloids and Surfaces A: Physicochemical and Engineering Aspects, 2011, vol. 382, pp. 154-164.
Gratton et al., "The effect of particle design on cellular internalization pathways", PNAS, Aug. 19, 2008, vol. 105, No. 33, pp. 11613-11618.
Khopade et al., "Ultrathin Antibiotic Walled Microcapsules", Biomacromolecules, 2005, vol. 6, pp. 229-234.
Lee et al., "Multidrug encapsulation by coaxial tri-capillary electrospray", Colloids and Surfaces B: Bionterfaces, 2011, vol. 82, pp. 104-110.
Pancholi et al., "In Vitro Method to Characterize Diffusion of Dye from Polymeric Particles: A Model for Drug Release", Langmuir, 2009, vol. 25, No. 17, pp. 10007-10013.

\* cited by examiner

LAYERED BODIES AND COMPOSITIONS CONTAINING THEM

This is a continuation application of U.S. application Ser. No. 13/984,345, filed under 35 U.S.C. § 371 on Oct. 14, 2013, published; which is the national stage entry of international application PCT/GB2012/050276, filed under the authority of the Patent Cooperation Treaty on Feb. 8, 2012, published; which claims priority to United Kingdom Application No. 1102148.2, filed on Feb. 8, 2011. The entire disclosures of all the aforementioned applications are expressly incorporated herein by reference for all purposes.

The present invention relates to layered bodies, which may be in capsule or thread form, that typically have a size in the micro- or nanometer scale.

BACKGROUND OF THE INVENTION

Micro- or nanometre scale multilayer particles, capsules and fibres are of increasing interest in a number of fields, including diagnostic and therapeutic applications. They can be used, for example, to deliver therapeutic agents, contrast agents, living cells, and other species to desired sites in vivo. Because of their small size, it is a considerable challenge to create the micro- or nanometre scale multilayer particles, capsules and fibres with specific properties. Some methods of manufacturing the micro- or nanoscale species, while appearing initially promising, have suffered from their requirement to use surfactants or certain additives. It would be desirable to produce micro- or nanometer scale multilayer particles, capsules and fibres without surfactants or potentially harmful additives.

One of the desirable uses of the micro- or nanometer scale multilayer capsules and fibres is as carriers for a specific agent, e.g. a therapeutic or diagnostic agent. Conventional carriers, e.g. those used in macroscale drug delivery applications, are limited in their performance for a number of reasons, and may not be suitable for use in the techniques for making the micro- or nanometer scale multilayer particles, capsules and fibres. Layer by layer deposition commonly requires selecting appropriate materials for adjacent layers so that they interact and adhere to one another, e.g. having adjacent layers comprising species of opposing charges or adjacent layers that rely on hydrogen bonding. Layer by layer deposition techniques are described, for example, in US 2005/0208100 and US 2005/0163714, both of which are incorporated herein by reference in their entirety. A drawback of layer by layer deposition is the considerable time it takes to produce the multilayered species, and the required use of certain material to produce the adherence between adjacent layers. Additionally, they typically use a crystalline material as a core, which leads to a non-spherical core in the final multilayered species.

Recent developments in producing micro- or nanometer scale multilayer capsules and fibres have been through the use of electrohydrodynamic processes. An example of such a process is described in J. R. Soc. Interface (2008) 5, 1255-1261, authored by Ahmad et al., which is incorporated herein by reference in its entirety. Such processes typically use a flowing medium that is subjected to an applied electric field. The process can result in a formation of a jet, which then breaks up into fine droplets or remains intact to produce a fibre or thread. The paper authored by Ahmad et al., mentioned above, describes an electrohydrodynamic process that employs three concentric needles. The needles typically have a diameter that is far larger (e.g. larger than 0.1 mm) than the capsules or fibres they can produce (having diameters in the micrometer and/or nanometer scale). While the process of Ahmed et al offered advantages over the prior art, it was limited in the types of multilayered structures it can produce.

Hollow particles of the micro or nanometer scale, sometimes termed microbubbles, have also been found useful in certain applications. They are sometimes used as contrast agents in ultrasound. Recent investigations have been made into the use of microbubbles for the treatment and assessment of cancer. This is achieved by loading a desired agent on the surface of the bubble or cavity, which collapses with the application of ultra-sound at the desired site, enabling site-specific release of the agent.

It would be desirable to provide alternative methods and products to those described in the prior art, ideally methods and products that overcome or mitigate at least one problem associated with the prior art, whether or not expressly mentioned herein.

SUMMARY OF THE INVENTION

In a first aspect, the present invention provides a layered body comprising:
a core region;
at least one intermediate layer disposed around the core region; and an outer layer disposed around the at least one intermediate layer,
wherein at least one of the at least one intermediate layers comprises a gas, the layered body having at least one dimension, measured across the body and through the core region, of 100 µm or less. In an embodiment, the layered body may be in the form of a capsule. In an embodiment, the layered body may be in the form of a thread. In the present context, "intermediate" indicates that a layer is disposed between the core region and the outer layer. The outer layer will typically encompass the whole of the core region, at least in a cross section of the body, and the intermediate layer or layers will be disposed between the outer layer and the core region In a second aspect, the present invention provides a layered body comprising:
a core region having a substantially circular cross section;
at least two intermediate layers disposed around the core region;
an outer layer disposed around the at least two intermediate layers, the layered body having at least one dimension, measured across the body and through the core region, of 100 µm or less. In an embodiment, the layered body may be in the form of a capsule. In an embodiment, the layered body may be in the form of a thread. In the present context, "intermediate" indicates that a layer is disposed between the core region and the outer layer. The outer layer will typically encompass the whole of the core region, at least in a cross section of the body, and the intermediate layer or layers will be disposed between the outer layer and the core region. "Substantially circular" can include a circular shape and non-circular shapes, such as an oval shape.

In a third aspect, the present invention provides an electrohydrodynamic device for producing one or more layered bodies,
the device comprising
at least four concentrically arranged, spaced apart hollow needles, the needles together defining a core channel, at least two intermediate concentrically disposed tubular channels, and an outer concentrically disposed tubular channel; and
a means for applying a voltage to the needles. In the present context, "intermediate" indicates that a channel is disposed concentrically between the core channel and the outer channel. "Concentrically", in the present context, indicates that intermediate channels surround the core channel and, in turn, the outer channel surrounds the intermediate channels; in an embodiment, all the channels may share the same geometric centre or axis, but this need not necessarily be the case.

In a fourth aspect, the present invention provides a process for producing one or more layered bodies, the process
comprising:
providing an electrohydrodynamic device, the device comprising at least three concentrically arranged, spaced apart hollow needles, the needles together defining a core channel, at least one intermediate concentrically disposed tubular channel, and an outer concentrically disposed tubular channel,
providing a first fluid medium comprising a liquid comprising a non-volatile component
providing a second fluid medium comprising or consisting of a volatile liquid,
passing the second fluid medium through an intermediate concentrically disposed tubular channel, and, at the same time,
passing the first fluid medium through each of the plurality of channels disposed adjacent to the intermediate concentrically disposed tubular channel through which the second fluid medium is passed,
and applying a voltage to the needles,
such that, on leaving the needles, one or more layered bodies is or are formed. The one or more layered bodies may be bodies according to the first aspect. In an embodiment, the device of this aspect comprises at least four concentrically arranged, spaced apart hollow needles, the needles together defining a core channel, at least two intermediate concentrically disposed tubular channels, and an outer concentrically disposed tubular channel, and the fluid medium passed through at least one of the at least two intermediate concentrically disposed tubular channels is the second fluid medium, and optionally the fluid medium passed through the core channel is the second fluid medium; and optionally the fluid medium passed through the remaining channels is selected from the first fluid medium and the second fluid medium and is preferably the first fluid medium. In the present context, "intermediate" indicates that a channel is disposed concentrically between the core channel and the outer channel. "Concentrically", in the present context, indicates that intermediate channels surround the core channel and, in turn, the outer channel surrounds the intermediate channels; in an embodiment, all the channels may share the same geometric centre or axis, but this need not necessarily be the case. The present invention further provides a layered body obtainable by the process according to the fourth aspect.

In a fifth aspect, the present invention provides a process for producing one or more layered bodies, the process comprising:
providing the electrohydrodynamic device according to the third aspect,
passing fluid mediums through the hollow core, the at least two intermediate concentrically disposed tubular channels, and the outer concentrically disposed tubular channel,
and applying a voltage to the needles,
such that, on leaving the needles, one or more layered bodies is or are formed. The one or more layered bodies may be one or more layered bodies according to the second aspect. In the present context, "intermediate" indicates that a channel is disposed concentrically between the core channel and the outer channel. The fluid mediums may be selected from a first fluid medium comprising a liquid comprising a non-volatile component and a second fluid medium comprising or consisting of a volatile liquid. "Concentrically", in the present context, indicates that intermediate channels surround the core channel and, in turn, the outer channel surrounds the intermediate channels; in an embodiment, all the channels may share the same geometric centre or axis, but this need not necessarily be the case. The present invention further provides a layered body obtainable by the process according to the fifth aspect.

In a sixth aspect, the present invention provides a composition comprising a plurality of bodies of the first aspect and/or a plurality of bodies of the second aspect.

The present inventors have found that the layered bodies of the first aspect have advantages over the prior art. They find use in many applications, such as drug delivery, catalysis and protecting sensitive agents. For example, it is considered that they can be used in ultrasound and can increase the non-linear effect of an ultrasound diagnostic. They can also have many layers, which could have differing properties, and, in some embodiments, a gas-containing core region and a gas-containing intermediate layer, which enables selective destruction of the layers, which may be used to release different active agents, e.g. therapeutic or diagnostic agents, at different times. The layered bodies of the second aspect have advantages over the prior art, especially multilayered bodies produced using layer-by-layer techniques. The layered bodies of the second aspect can be formed much quicker than those of the layer-by-layer techniques, for example in electrohydrodynamic processes, e.g. a process of the fourth or fifth aspect. The removal of the core region in layer-by-layer formed bodies also involves techniques that can be detrimental to the bodies and/or involve agents that could be harmful if the layered body is used as a pharmaceutical, whereas the layered bodies produced in accordance with the present invention can avoid such difficulties. The present inventors have also found that the processes described herein allow a greater control of the thickness of the various layers, and therefore the volume of material in the various layers, than at least some of the processes described in the prior art. This can be of importance when aiming to standardise the content of the layered bodies produced in accordance with the processes of the present invention, which has particular importance in the pharmaceutical use of the layered bodies, such that rate of degradation and release of any therapeutic or diagnostic agents can be more accurately predicted. The control of the thickness of layers is also advantageous in being able to more closely control the energy absorption characteristics of the layered bodies, which can be useful in ultrasound applications.

DETAILED DESCRIPTION

In a first aspect, the present invention provides a layered body comprising:

a core region;

at least one intermediate layer disposed around the core region; and an outer layer disposed around the at least one intermediate layer, wherein at least one of the at least one intermediate layers comprises a gas, the layered body having at least one dimension, measured across the body and through the core region, of 100 μm or less. The core region may have a substantially circular cross section. The layered body of the first aspect may be producible from the process of fourth aspect. This has typically been found to produce a core region having a substantially circular cross section. In an embodiment, the at least one intermediate layer least partially surrounds, optionally completely surrounds, the core region. In an embodiment, the outer layer at least partially surrounds, optionally completely surrounds, the at least one intermediate layer. In an embodiment, the outer layer surrounds at least part of, optionally all of the, the core region. Typically, the at least one intermediate layer and the outer layer share the same core region. In an embodiment, the at least one intermediate layer and the outer layer are disposed concentrically around the core region. In an embodiment, "disposed concentrically", indicates that the at least one intermediate layer surrounds the core region and the outer layer surrounds the at least one intermediate layer; "disposed concentrically" covers embodiments where the core region is circular in cross section and non-circular in cross section. In an embodiment, "disposed concentrically" indicates that the core region and the at least one intermediate layer share the same core, but they need not necessarily share the same geometric centre (for example when the body is in the form of a capsule) or axis (for example when in the body is in the form of a thread).

In an embodiment in which there are two or more intermediate layers, preferably, the intermediate layer disposed closest to the core is surrounded at least partially, optionally completely, by the other intermediate layer or layers. In an embodiment in which there are two or more intermediate layers, the outer layer preferably at least partially, optionally completely, surrounds the intermediate layers.

The core region may be any suitable shape. It may or may not have a circular cross section. It may or may not have an oval cross section. The core region may or may not be spherical or approximately spherical in shape. The core region may have a shape selected from spherical, substantially spherical, spheroid, ellipsoidal and substantially ellipsoid. The core region may be elongated in shape.

Figure 7:
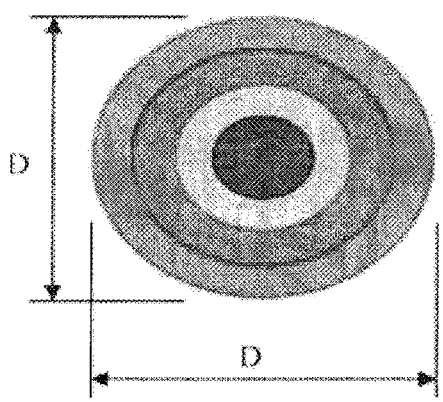
FIG. 7 shows the cross section of either capsule or a thread and how the diameter of the capsule or thread can be measured, for example either at the widest point (horizontal diameter in this Figure) or at its narrowest point (vertical diameter in this Figure).

In an embodiment, the layered body may be in the form of a capsule. The core region of the capsule may have a shape selected from spherical, substantially spherical, spheroid, ellipsoidal and substantially ellipsoid. The capsule may have core region that is encompassed, e.g. partially or entirely, by the least one intermediate layer, which, in turn, is or are (if there is more than one intermediate layer) encompassed by the outer layer. The capsule may have a substantially spherical core region, with the at least one intermediate layer and the outer layer in the form of approximate spheres arranged around, e.g. concentrically around, the core region. If the body is in the form of a capsule, the at least one dimension measured across the body may be the diameter across the capsule, optionally the largest diameter. The measurement may be made for example by obtaining an image of the capsule using a suitable means, such as scanning electron microscopy, and measuring the diameter across the capsule. This is illustrated on a schematic drawing of a layered body in FIG. 7. Optionally, the diameter of the body can be measured at its widest point (horizontal diameter in FIG. 7) or at its narrowest point (vertical diameter in FIG. 7).

In an embodiment, the layered body may be in an elongated form. The body may have an elongated core, with the at least one intermediate layer disposed around, e.g. radially around, the elongated core, and the outer layer disposed around, e.g. radially around, the at least one intermediate layer. The at least one intermediate layer may extend along at least part of, optionally the whole of, the length of the core region. The outer layer may extend along at least part of, optionally whole of, the length of the core region. When the body is elongate, it may have two opposing ends. The at least one intermediate layer may or may not cover one or both ends of the core region of elongate body. The outer layer may or may not cover one or both ends of elongate body. The body may have an elongated core having an axis, and the at least one intermediate layer and the outer layer being disposed around, e.g. radially around, the axis, with the intermediate layer being disposed between the outer layer and the core region. The body may have an elongated core region having an axis, and the at least one intermediate layer and the outer layer being disposed concentrically around, the axis. The elongated form may, for example, be in the form of an elongated particle or in the form of a thread. If the body is in elongated form having an axis the at least one dimension measured across the body may be a diameter of the elongated form, measured in a direction perpendicular to the axis. If the body is in the form of a thread, the at least one dimension measured across the body may be the diameter of the thread. The measurement may be made for example by obtaining an image of the thread using a suitable means, such as a scanning electron microscopy, and measuring the diameter of the thread.

In an embodiment, the core region and the outer layer each independently comprises a solid or a liquid medium, and the at least one intermediate layer comprises a gas. In an embodiment, the body comprises at least two intermediate layers, the core region and the outer layer each independently comprises a solid or a liquid medium, at least one of the intermediate layers comprises a gas and at least one of the intermediate layers comprises a solid or liquid medium.

In an embodiment, at least two intermediate layers are disposed around, optionally concentrically around, the core region. In an embodiment, the core comprises or consists of a gas. In an embodiment, an intermediate layer disposed adjacent the core region defines a hollow core region, and the hollow core region comprises or consists of a gas. In an embodiment, at least two intermediate layers are disposed around, optionally concentrically around, the core region, an intermediate layer disposed adjacent the core region defines a hollow core region, the hollow core region comprising a gas, and one or more of the other intermediate layers comprises a gas. The layered body may be formed according to the process of the fourth or fifth aspect and the gas in the at least one intermediate layer, and optionally in the core region (if it contains a gas), may comprise (i) a gas from the environment into which the fluid mediums pass into when exiting the channels and/or (ii) a gas formed from the vaporisation of the volatile liquid of the second fluid medium, which may be as described herein.

In an embodiment, the core region comprises or consists of a first gas, at least two intermediate layers are disposed around, optionally concentrically around, the core region, the intermediate layer disposed adjacent the core region comprising a solid or a liquid medium, and at least one of the further outwardly disposed intermediate layers comprises a second gas. The first and second gas may be the same or different.

In a second aspect, the present invention provides a layered body comprising:
 a core region having a substantially circular cross section;
 at least two intermediate layers disposed around the core region;
 an outer layer disposed around the at least two intermediate layers,
 the layered body having at least one dimension, measured across the body and through the core region, of 100 µm or less. In an embodiment, the layered body may be in the form of a capsule. In an embodiment, the layered body may be in the form of a thread. The layered body of the second aspect may be producible from the process of the fifth aspect. This has typically been found to produce a core region having a substantially circular cross section. In an embodiment, one of the intermediate layers least partially surrounds, optionally completely surrounds, the core region. Optionally, the intermediate layer disposed closest to the core is surrounded at least partially, optionally completely, by the other intermediate layer or layers. The outer layer preferably at least partially, optionally completely, surrounds the intermediate layers. In an embodiment, the outer layer surrounds at least part of, optionally all of the, the core region. In an embodiment, the at least two intermediate layers and the outer layer share the same core region. In an embodiment, the at least two intermediate layers and the outer layer are disposed concentrically around the core region. In an embodiment, "disposed concentrically", indicates that the at least two intermediate layers surround the core region and the outer layer surrounds the at least two intermediate layers; "disposed concentrically" covers embodiments where the core region is circular in cross section and non-circular in cross section. In an embodiment, "disposed concentrically" indicates that the core region and the at least two intermediate layers share the same core, but they need not necessarily share the same geometric centre or axis.

In an embodiment, the core region comprises or consists of a gas. In an embodiment, an intermediate layer disposed adjacent the core region defines a hollow core region, and the hollow core region comprises or consists of a gas.

In an embodiment, at least one of the at least two intermediate layers comprises a gas.

In an embodiment, the core region and at least one of the at least two intermediate layers comprise a gas.

Preferably, the gas in the at least one intermediate layer and/or the core region comprises a gas selected from oxygen and nitrogen.

At least one of the core region, the intermediate layer or layers and the outer layer may comprise one or more solid or liquid substances. At least one of the core region, the intermediate layer or layers and the outer layer may comprise one or more pharmaceutically acceptable substances. The one or more solid or liquid substances may be carrier substances, suitable for acting as carriers for one or more active agents, optionally agents selected from diagnostic and therapeutic agents. The one or more solid or liquid substances may be or comprise an organic substance, optionally a polymer. The one or more solid or liquid substances preferably comprise a biocompatible carrier substance. The one or more solid or liquid substances may be selected from poly(lactic-co-glycolic acid) (PLGA), polycaprolactone (PCL), polymethylsilsesquioxane (PMSQ), perfluorohexane (PFH), perfluoropentane (PFP), polyurethane, starch, albumin, polyethylene oxide (PEO), glycerol and oil, such as olive oil.

Particularly preferred polymers include, but are not limited to sodium polystyrene sulfonate (PSS), polyethers, such as a polyethylene oxide (PEO), polyoxyethylene glycol or polyethylene glycol (PEG), polyethylene imine (PEI), a biodegradable polymer such as a polylactic acid, polycaprolactone, polyglycolic acid, poly(lactic-co-glycolic acid) (PLGA), polymethylsilsesquioxane (PMSQ) and copolymers, derivatives, and mixtures thereof. Other polymers that may be used include those well known to those of skill in the art to be used in cell cultures, implants, regenerative, therapeutic, and pharmaceutical compositions. One such example is polyvinylpyrrolidone (PVP).

Optionally, the polymer may have a property selected from: being positively-charged being (cationic), being negatively-charged (anionic), being polyethylene glycol(PEG)-ylated, being covered with a zwitterion, being hydrophobic, being superhydrophobic (for example having with water contact angles in excess of 150°), being hydrophilic, being superhydrophilic (for example, where the water contact angle is near or at 0°), being olephobic/lipophobic, being olephilic/lipophilic, and/or nanostructured, among others.

The polymer may be a water-soluble and/or hydrophilic polymer, which may be selected from biocompatible polymers, including, but not limited to, cellulose ether polymers, including those selected from the group consisting of hydroxyl alkyl cellulose, including hydroxypropyl methyl cellulose (HPMC), hydroxypropyl cellulose (HPC), hydroxyethyl cellulose (HEC), methyl cellulose (MC), carboxymethyl cellulose (CMC), and mixtures thereof.

The polymer may also be selected from polyvinylpyrrolidone, vinyl acetate, polyvinylpyrrolidone-vinyl acetate copolymers, polyvinyl alcohol (PVA), acrylates and polyacrylic acid (PAA), including polyacrylate polymer, vinylcaprolactam/sodium acrylate polymers, methacrylates, poly(acryl amide-co-acrylic acid) (PAAm-co-AA), vinyl acetate and crotonic acid copolymers, polyacrylamide, polyethylene phosphonate, polybutene phosphonate, polystyrene, polyvinylphosphonates, polyalkylenes, and carboxy vinyl polymer. The multiphasic fiber compositions may comprise derivatives, copolymers, and further combinations of such polymers, as well.

The polymer may be selected from water insoluble or hydrophobic polymers including, but not limited to, cellulose acetate, cellulose nitrate, ethylene-vinyl acetate copolymers, vinyl acetate homopolymer, ethyl cellulose, butyl cellulose, isopropyl cellulose, shellac, hydrophobic silicone polymer (e.g., dimethylsilicone), polymethyl methacrylate (PMMA), cellulose acetate phthalate and natural or synthetic rubber; siloxanes, such as polydimethylsiloxane (PMDS), cellulose, polyethylene, polypropylene, polyesters, polyurethane and nylon, including copolymers, derivatives, and combinations thereof.

The polymers may be crosslinked, optionally after formation of the body, for example by the application of heat, ionizing radiation or other methods of curing and treating polymers known to those of skill in the art.

Optionally, the polymer may be selected from sodium alginate, carrageenan, xanthan gum, gum acacia, Arabic gum, guar gum, pullulan, agar, chitin, chitosan, pectin, karaya gum, locust bean gum, various polysaccharides; starches such as maltodextrin, amylose, corn starch, potato starch, rice starch, tapioca starch, pea starch, sweet potato starch, barley starch, wheat starch, modified starch (e.g., hydroxypropylated high amylose starch), dextrin, levan, elsinan and gluten; and proteins such as collagen, whey protein isolate, casein, milk protein, soy protein, keratin, and gelatin.

The layered body may comprise an active agent, for example in one or more of the core region, the intermediate layer or layers or the outer layer. The active agent in the body may be selected from pharmaceutical and/or cosmetic active agents, which may be selected from growth factors; growth factor receptors; transcriptional activators; translational promoters; antiproliferative agents; growth hormones; anti-rejection drugs; anti-thrombotic agents; anti-coagulants; stem cell or gene therapies; antioxidants; free radical scavengers; nutrients; co-enzymes; ligands; cell adhesion peptides; peptides; proteins; nucleic acids; DNA; RNA; sugars; saccharides; nutrients; hormones; antibodies; immunomodulating agents; growth factor inhibitors; growth factor receptor antagonists; transcriptional repressors; translational repressors; replication inhibitors; inhibitory antibodies; cytotoxin; hormonal agonists; hormonal antagonists; inhibitors of hormone biosynthesis and processing; antigestagens; antiandrogens; anti-inflammatory agents; non-steroidal antiinflammatory agents (NSAIDs); analgesics; COX-I and II inhibitors; antimicrobial agents; antiviral agents; antifungal agents; antibiotics; anti-proliferative agents; antineoplastic/antiproliferative/anti-miotic agents; anesthetic, analgesic or pain-killing agents; antipyretic agents, prostaglandin inhibitors; platelet inhibitors; DNA de-methylating agents; cholesterol-lowering agents; vasodilating agents; endogenous vasoactive interference agents; angiogenic substances; cardiac failure active ingredients; polysaccharides; sugars; targeting toxin agents; aptamers; quantum dots; nano-materials; nano-crystals; and combinations thereof.

The layered body may comprise a diagnostic agent, for example in one or more of the core region, the intermediate layer or layers or the outer layer. The diagnostic agent in the body may be an agent suitable for use in a technique selected from, but not limited to, diagnostic medical imaging procedures (for example, radiographic imaging (x-ray), fluorescence spectroscopy, Forster/fluorescent resonance energy-transfer (FRET), computed tomography (CT scan), magnetic resonance imaging (MRI), positron emission tomography (PET), other nuclear imaging, and the like. The diagnostic agent may be an agent for use in diagnostic imaging, for example a contrast agents, such as barium sulfate for use with MRI, for example, or fluorescein isothiocyanate (FITC).

At least one of the core region, the intermediate layer or layers, and the outer layer may comprise an active agent selected from a diagnostic agent and a therapeutic agent. The diagnostic agent may be selected from, for example, contrast agents, e.g. contrast agents for use in MRI techniques, and luminescent agents, e.g. fluorescent agents. The therapeutic agent may be a drug for the treatment or prevention of a disease. Optionally at least one or the core region, the intermediate layer or layers, and the outer layer may comprises an agent selected from a peptide, DNA and RNA.

Suitable active agents for use in such pharmaceutically and/or cosmetically acceptable compositions are well known to those of skill in the art and include, by way of non-limiting example, those disclosed in the Merck Index, An Encyclopedia of Chemicals, Drugs, and Biologicals, Thirteenth Edition (2001) by Merck Research Laboratories and the International Cosmetic Ingredient Dictionary and Handbook, Tenth Ed., 2004 by Cosmetic Toiletry and Fragrance Association, and U.S. Pat. Nos. 6,589,562, 6,825,161, 6,063,365, and 6,491,902, all to Shefer et al, each incorporated herein by reference.

Optionally, at least one of the core region, the intermediate layer or layers, and the outer layer may comprise a diagnostic agent and another of the core region, the intermediate layer or layers, and the outer layer comprises a therapeutic agent.

The at least one dimension, measured across the body and through the core region, is 100 µm or less, optionally 50 µm or less, optionally 30 µm or less, optionally 20 µm or less, optionally 10 µm or less, optionally 1 µm or less, optionally 500 nm or less, optionally 200 nm or less. It the body is in the form of a capsule, the dimension may be the diameter of the capsule, optionally the diameter of the capsule at its widest point. It the body is in the form of a thread, the dimension may be the diameter of the thread, optionally the diameter of the thread at its widest point. The measurement of the dimension may be made for example by obtaining an image of the body using a suitable means, such as scanning electron microscopy, and measuring the dimension across the body.

In a third aspect, the present invention provides an electrohydrodynamic device for producing one or more layered bodies, the device comprising at least four concentrically arranged, spaced apart hollow needles, the needles together defining a core channel, at least two intermediate concentrically disposed tubular channels, and an outer concentrically disposed tubular channel; and a means for applying a voltage to the needles.

The needles are able to be charged by applying a voltage to the needles. The needles are preferably made from an electrically conducting material, preferably a metal. The metal may be selected from, for example, an elemental metal or a metal alloy. The metal may, for example, comprise steel.

The innermost needle in the device, which defines the hollow core, may have an inner diameter of at least 0.01 mm, preferably at least 0.1 mm. The innermost needle in the device, which defines the hollow core, may have an inner diameter of from 0.01 mm to 2 mm, optionally from 0.05 to 1.5 mm, optionally from 0.15 to 1.0 mm, optionally from 0.15 to 0.25 mm, optionally about 0.2 mm.

The space between the outer surface of a needle and the inner surface of the outwardly disposed adjacent needle may be from 0.01 mm to 1.5 mm, preferably 0.1 mm to 1 mm, optionally 0.2 to 0.9 mm, optionally 0.3 to 0.7 mm, optionally about 0.5 mm Optionally the space between the outer surface of each needle (except the outer needle) and the inner surface of the outwardly disposed adjacent needle may be from 0.01 mm to 1.5 mm, preferably 0.1 mm to 1 mm, optionally 0.2 to 0.9 mm, optionally 0.3 to 0.7 mm, optionally about 0.5 mm.

In an embodiment, the device comprises an inner needle, which defines the hollow core, which has an inner diameter of from 0.15 to 1.0 mm, optionally from 0.15 to 0.25 mm, optionally about 0.2 mm, at least three needles disposed outwardly in a concentric manner from the innermost needle, wherein the space between the outer surface of each needle (except the outer needle) and the inner surface of the outwardly disposed adjacent needle is from 0.01 mm to 1.5 mm, preferably 0.1 mm to 1 mm, optionally 0.2 to 0.9 mm, optionally 0.3 to 0.7 mm, optionally about 0.5 mm.

The means for applying a voltage to the needles may apply any suitable voltage. The voltage may be from 1 kV to 50 kV, preferably 3 kV to 30 kV, more preferably 15 kV to 25 kV, optionally about 20 kV. The means for supplying a voltage may apply a dc voltage or an ac voltage. A ground electrode may be present, which may be at or near the collection means. Optionally the ground electrode is a ring electrode, which may be placed such that the centre of the ring is along the axis formed by the innermost needle. The ground electrode may be placed at any suitable distance from the needles, for example a distance of from 1 mm to 1 m, optionally 1 mm to 50 cm, optionally 1 mm to 10 cm, optionally 1 mm to 20 mm, optionally 5 mm to 15 mm, optionally about 12 mm.

The device optionally further comprises means for supplying a fluid to each channel. The means for supplying a fluid to each channel preferably can supply a fluid medium selected from the first and second fluid medium. Preferably, at least one of the intermediate concentrically disposed channels is in fluid connection with a means for supplying the first fluid medium; and optionally the remaining channels are in fluid connection with a fluid medium selected from the first fluid medium and the second fluid medium. The means for supplying a fluid to each channel preferably comprises a syringe pump. Preferably a syringe pump is in fluid connection with one end of each channel. Each means for supplying a fluid can preferably supply a fluid medium at a rate of from 1 µl/min to 2000 µl/min, optionally from 50 to 1000 µl/min, optionally from 100 to 800 µl/min.

Optionally, the device further comprises a collection means for collecting the fluid mediums exiting the needles and/or the layered body or bodies formed therefrom. The collection means is preferably earthed. The collection means may be a receptacle.

The device may further comprise a means for observing the fluid mediums exiting the needles and/or the layered body or bodies formed therefrom. The means for observing may comprise a camera, optionally connected to a recording means. The camera may optionally be connected to a visual display means, so that the fluid mediums exiting the needles and/or the layered body or bodies formed therefrom exiting the needles can be observed.

In a fourth aspect, the present invention provides a process for producing one or more layered bodies, the process comprising:

providing an electrohydrodynamic device, the device comprising at least three concentrically arranged, spaced apart hollow needles, the needles together defining a core channel, at least one intermediate concentrically disposed tubular channel, and an outer concentrically disposed tubular channel, a means for applying a voltage to the needles, providing a first fluid medium comprising a liquid comprising a non-volatile component providing a second fluid medium comprising or consisting of a volatile liquid, passing the second fluid medium through an intermediate concentrically disposed tubular channel, and, at the same time, passing the first fluid medium through each of the plurality of channels disposed adjacent to the intermediate concentrically disposed tubular channel through which the second fluid medium is passed, and applying a voltage to the needles, such that, on leaving the needles, one or more layered bodies is or are formed. This method involves passing the first fluid medium through each of the plurality of channels disposed adjacent to the intermediate concentrically disposed tubular channel through which the second fluid medium is passed. If the device comprises three concentrically arranged, spaced apart hollow needles, it has a core channel, a single intermediate concentrically disposed tubular channel, and an outer channel, with the core channel and the outer channel being disposed adjacent to the intermediate concentrically disposed tubular channel. Accordingly, if the device comprises three concentrically arranged, spaced apart hollow needles, the second fluid medium is passed through the intermediate concentrically disposed tubular channel, and the first fluid medium is passed through the core channel and the outer concentrically disposed tubular channel.

In an embodiment, the device of this aspect comprises at least four concentrically arranged, spaced apart hollow needles, the needles together defining a core channel, at least two intermediate concentrically disposed tubular channel, and an outer concentrically disposed tubular channel, and the fluid medium passed through at least one of the at least two intermediate concentrically disposed tubular channels is the second fluid medium, and optionally the fluid medium passed through the core channel is the second fluid medium.

In a fifth aspect, the present invention provides a process for producing one or more layered bodies, the process comprising:

providing the electrohydrodynamic device according to the third aspect, passing fluid mediums through the hollow core, the at least two intermediate concentrically disposed tubular channels, and the outer concentrically disposed tubular channel, and applying a voltage to the needles, such that, on leaving the needles, one or more layered bodies is or are formed. The fluid mediums may be selected from a first fluid medium comprising a liquid comprising a non-volatile component and a second fluid medium comprising or consisting of a volatile liquid.

The processes of the fourth or fifth aspect may be electrohydrodynamic processes. As the fluid mediums leave the needles, typically a jet of the fluid mediums is formed, which then either breaks up into capsules or remains intact to produce a thread.

The first fluid medium comprises a liquid comprising a non-volatile component. The liquid of the first fluid medium may be the non-volatile component. The liquid may have a boiling point of at least 100° C., optionally at least 150° C., optionally at least 200° C., optionally at least 250° C. All boiling and melting points given herein, unless otherwise stated, are measured at standard pressure (101.325 kPa). The liquid may comprise an organic solvent. The organic solvent may comprise a non-polar solvent and/or a polar solvent. The organic solvent may comprise an aprotic solvent and/or a protic solvent. Non-polar solvents include, but are not limited to, pentane, cyclopentane, hexane, benzene, toluene, 1,4-dioxane, chloroform, and diethylether. The solvent may comprise a polar aprotic solvent, optionally selected from dichloromethane, tetrahydrofuran, ethylacetate, acetone, dimethylformamide, acetonitrile, dimethyl sulphoxide. The solvent may comprise a polar protic solvent, optionally selected from formic acid, n-butanol, isopropanol, n-propanol, ethanol, methanol and acetic acid. The organic solvent may comprise a hydrocarbon. The hydrocarbon may comprise an aromatic or an aliphatic hydrocarbon. The hydrocarbons may be selected from, but are not limited to, pentane, cyclopentane, hexane, cyclohexane and benzene.

The first fluid medium preferably has a dynamic viscosity of 1.5 mPas or more, optionally a dynamic viscosity of 1.6 mPas or more, optionally a dynamic viscosity of 1.7 mPas or more. The dynamic viscosity is measured at standard temperature (25° C.) and pressure (101.325 kPa). The dynamic viscosity of the first fluid medium is preferably more than the dynamic viscosity of the second fluid medium, when measured under the same conditions. Dynamic viscosity values can be measured according to a standard method known to those skilled in the art, for example by using a U-tube viscometer or a rotational viscometer, such as a commercially available VISCOEASY rotational viscometer. Ethanol may used as a calibrating medium in the relevant measurement equipment, if necessary.

The first fluid medium preferably has a surface tension of 20 $mNm^{-1}$ or more, optionally 25 $mNm^{-1}$ or more, optionally 30 $mNm^{-1}$ or more. The first fluid medium preferably has a surface tension of 20 $mNm^{-1}$ to 30 $mNm^{-1}$. The surface tension of the first fluid medium is measured at standard temperature (25° C.) and pressure (101.325 kPa). The surface tension of the first fluid medium is preferably more than the surface tension of the second fluid medium, when measured under the same conditions. Surface tension can be measured according to a standard method known to those skilled in the art, for example by using a tensiometer, e.g. a commercially available Kruss Tensiometer. Ethanol may used as a calibrating medium in the relevant measurement equipment, if necessary.

The conductivity of the first fluid medium is preferably $1 \times 10^{-8}$ $Sm^{-1}$ or more, optionally $1 \times 10^{-7}$ $Sm^{-1}$ or more, optionally $1 \times 10^{-6}$ $Sm^{-1}$ or more, optionally $1 \times 10^{-5}$ $Sm^{-1}$ or more. Conductivity in this context refers to the electrical conductivity. The conductivity of the first fluid medium is measured at standard temperature (25° C.) and pressure (101.325 kPa). The conductivity of the first fluid medium is preferably more than the conductivity of the second fluid medium, when measured under the same conditions. Conductivity can be measured according to a standard method known to those skilled in the art, for example by using a conductivity probe, such as the commercially available HI-8733 conductivity probe, available from Sigma-Aldrich. Ethanol may used as a calibrating medium in the relevant measurement equipment, if necessary.

The liquid of the first fluid medium may be any suitable liquid in which a non-volatile component, e.g. a polymer, can be dissolved and/or suspended. The non-volatile component, e.g. a polymer, may be completely dissolved in the liquid of the first fluid medium. The non-volatile component may be an organic substance, optionally a polymer. The non-volatile component preferably has a melting point of at least 100° C., optionally at least 150° C., optionally at least 200° C., optionally at least 250° C. The non-volatile component preferably comprises a polymer. The non-volatile component, e.g. a polymer, may be present in the liquid of the first fluid medium in an amount of at least 1% by weight, preferably at least 10% by weight, optionally at least 20% by weight, optionally at least 40% by weight, optionally at least 50% by weight, optionally at least 60% by weight, optionally at least 70% by weight, optionally at least 80% by weight. It has been found that if at least one of the fluid mediums comprises at least 60% by weight of a polymer, particularly the fluid medium passed down the outer concentrically disposed channel, the formation of a layered body in the form of a thread is promoted. Likewise, it has been found if at least one of the fluid mediums comprises less than 60% by weight of a polymer, particularly the fluid medium passed down the outer concentrically disposed channel, the formation of layered bodies in the form of capsules is promoted. Accordingly, in an embodiment, at least one of the fluid mediums, optionally the fluid medium passed down the outer concentrically disposed channel, comprises a polymer in an amount of 60% by weight or more. Accordingly, in an embodiment, at least one of the fluid mediums, optionally the fluid medium passed down the outer concentrically disposed channel, comprises a polymer in an amount of less than 60% by weight.

Particularly preferred polymers for use in the first fluid medium include, but are not limited to sodium polystyrene sulfonate (PSS), polyethers, such as a polyethylene oxide (PEO), polyoxyethylene glycol or polyethylene glycol (PEG), polyethylene imine (PEI), a biodegradable polymer such as a polylactic acid, polycaprolactone, polyglycolic acid, poly(lactic-co-glycolic acid) (PLGA), polymethylsilsesquioxane (PMSQ) and copolymers, derivatives, and mixtures thereof. Other polymers that may be used include those well known to those of skill in the art to be used in cell cultures, implants, regenerative, therapeutic, and pharmaceutical compositions. One such example is polyvinylpyrrolidone (PVP).

Optionally, the polymer for use in the first fluid medium may have a property selected from: being positively-charged being (cationic), being negatively-charged (anionic), being polyethylene glycol(PEG)-ylated, being covered with a zwitterion, being hydrophobic, being superhydrophobic (for example having with water contact angles in excess of 150°), being hydrophilic, being superhydrophilic (for example, where the water contact angle is near or at 0°), being olephobic/lipophobic, being olephilic/lipophilic, and/or nanostructured, among others.

The polymer for use in the first fluid medium may be a water-soluble and/or hydrophilic polymers, which may be selected from biocompatible polymers, including, but not limited to, cellulose ether polymers, including those selected from the group consisting of hydroxyl alkyl cellulose, including hydroxypropyl methyl cellulose (HPMC), hydroxypropyl cellulose (HPC), hydroxyethyl cellulose (HEC), methyl cellulose (MC), carboxymethyl cellulose (CMC), and mixtures thereof.

The polymer for use in the first fluid medium may also be selected from polyvinylpyrrolidone, vinyl acetate, polyvinylpyrrolidone-vinyl acetate copolymers, polyvinyl alcohol (PVA), acrylates and polyacrylic acid (PAA), including polyacrylate polymer, vinylcaprolactam/sodium acrylate polymers, methacrylates, poly(acryl amide-co-acrylic acid)

(PAAm-co-AA), vinyl acetate and crotonic acid copolymers, polyacrylamide, polyethylene phosphonate, polybutene phosphonate, polystyrene, polyvinylphosphonates, polyalkylenes, and carboxy vinyl polymer. The multiphasic fiber compositions may comprise derivatives, copolymers, and further combinations of such polymers, as well.

The polymer for use in the first fluid medium may be selected from water insoluble or hydrophobic polymers including, but not limited to, cellulose acetate, cellulose nitrate, ethylene-vinyl acetate copolymers, vinyl acetate homopolymer, ethyl cellulose, butyl cellulose, isopropyl cellulose, shellac, hydrophobic silicone polymer (e.g., dimethylsilicone), polymethyl methacrylate (PMMA), cellulose acetate phthalate and natural or synthetic rubber; siloxanes, such as polydimethylsiloxane (PMDS), cellulose, polyethylene, polypropylene, polyesters, polyurethane and nylon, including copolymers, derivatives, and combinations thereof.

The polymers for use in the first fluid medium may be crosslinked, optionally after formation of the body, for example by the application of heat, ionizing radiation or other methods of curing and treating polymers known to those of skill in the art.

Optionally, the polymer for use in the first fluid medium may be selected from sodium alginate, carrageenan, xanthan gum, gum acacia, Arabic gum, guar gum, pullulan, agar, chitin, chitosan, pectin, karaya gum, locust bean gum, various polysaccharides; starches such as maltodextrin, amylose, corn starch, potato starch, rice starch, tapioca starch, pea starch, sweet potato starch, barley starch, wheat starch, modified starch (e.g., hydroxypropylated high amylose starch), dextrin, levan, elsinan and gluten; and proteins such as collagen, whey protein isolate, casein, milk protein, soy protein, keratin, and gelatin.

If a first fluid medium, as described herein, is passed through two adjacent channels, preferably, the first fluid mediums in one of these channels is immiscible with the first fluid medium in the adjacent channel. The first fluid mediums should be sufficiently immiscible such that two distinct phases form in the layered bodies. A person skilled in the art of electrohydrodynamic techniques could select appropriate first fluid mediums.

The second fluid medium comprises or consists of a volatile liquid. In an embodiment, the volatile liquid is a liquid that has a boiling point not higher than 50° C. above the temperature of the environment into which the fluid mediums pass into when exiting the channels, optionally not higher than 40° C. above the temperature of the environment into which the fluid mediums pass into when exiting the channels, optionally not higher than 35° C. above the temperature of the environment into which the fluid mediums pass into when exiting the channels, optionally not higher than 30° C. above the temperature of the environment into which the fluid mediums pass into when exiting the channels. For example, if the temperature of the environment into which the fluid mediums pass into when exiting the channels is 25° C., preferably, the volatile liquid has a boiling point of 75° C. or less. The volatile liquid may have a boiling point of less than 100° C., optionally less than 80° C., optionally less than 70° C., optionally less than 60° C., optionally less than 50° C.

The temperature of the environment into which the fluid mediums pass into when exiting the channels may be any suitable temperature. The process may be carried out such that the temperature of the environment into which the fluid mediums pass into when exiting the channels is at or above the boiling point of the liquid of the second fluid medium. The temperature of the environment into which the fluid mediums pass into when exiting the channels may be above 15° C., optionally above 20° C., optionally above 25° C. The temperature of the environment into which the fluid mediums pass into when exiting the channels may be less than 150° C., optionally less than 100° C., optionally less than 80° C., optionally less than 60° C., optionally less than 40° C. The temperature of the environment into which the fluid mediums pass into when exiting the channels may be from 10 to 40° C., optionally from 20 to 30° C. It has been surprisingly found that when a second fluid medium as described herein is passed down the intermediate channel (with the first fluid medium being passed down the other channels as described herein), a layered body is formed that has a intermediate layer comprising a gas.

The environment into which the fluid mediums pass into when exiting the channels may or may not contain a gas. Preferably, the environment into which the fluid mediums pass into when exiting the channels contains a gas, which may comprise a gas selected from nitrogen, oxygen, and a gas from Group 18 of the periodic table. The gas from Group 18 of the periodic table may be selected from helium, neon and argon. The environment into which the fluid mediums pass into when exiting the channels may contain air.

The environment into which the fluid mediums pass into when exiting the channels may contain a gas and be at a pressure of from 80 kPa to 120 kPa, optionally 90 to 110 kPa, optionally 95 to 105 kPa, optionally around standard pressure (101.325 kPa).

The volatile liquid may be selected from a non-polar liquid, a polar aprotic liquid, and polar protic solvents. Preferably, the volatile liquid comprises or is a perhalocarbon, most preferably a perfluorocarbon. Perhalocarbons are organic compounds consisting of carbon and halogen atoms. Perfluorocarbons are organic compounds consisting of carbon and fluorine atoms. Preferably the perhalocarbon, e.g. the perfluorocarbon, contains 10 carbon atoms or less, optionally 9 carbons atoms or less, optionally 8 carbons atoms or less, optionally 7 carbons or less, optionally 6 carbons or less, optionally 5 carbons or less, optionally 4 carbons or less. Preferably the perhalocarbon, e.g. the perfluorocarbon, contains 3 or more carbon atoms, optionally 4 or more carbon atoms. The perfluorocarbon may be selected from, but is not limited to, octafluoropropane, perfluorohexane, perfluoropentane, and perfluorodecalin.

The volatile liquid may comprise a halogenated hydrocarbon, which may be selected from, but is not limited to, a halogenated alkane, halogenated alkene and halogenated alkyne. The hydrocarbon may be branched or linear, and optionally substituted with one or more substituents other than a halogen. The halogenated hydrocarbon may have one or more halogens on each molecule, which may be selected from fluorine, chlorine, bromine and iodine. The halogenated hydrocarbon is preferably a fluoroalkyl. The halogenated hydrocarbon may contain 10 carbons or less, optionally 9 carbons atoms or less, optionally 8 carbons atoms or less, optionally 7 carbons or less, optionally 6 carbons or less, optionally 5 carbons or less, optionally 4 carbons or less. The halogenated hydrocarbon may contain 3 or more carbon atoms, optionally 4 or more carbon atoms.

Optionally, the volatile liquid comprises a heterofluoroalkyl. Examples of heterofluoroalkyls include, but are not limited to, methoxynonafluorobutane and ethoxynonofluorobutane.

The volatile solvent may comprise an organic solvent selected from, but not limited to, ethanol, acetone, ethyl acetate, acetates, alcohol, ether, aliphatic, aromatic hydrocarbons, chlorinated hydrocarbons, ketones and chloroform.

The second fluid medium preferably has a dynamic viscosity of 1.3 mPas or less, optionally a dynamic viscosity of 1.2 mPas or less, optionally a dynamic viscosity of 1.1 mPas or less. The dynamic viscosity is measured at standard temperature (25° C.) and pressure (101.325 kPa). Dynamic viscosity values can be measured according to a standard method known to those skilled in the art, for example by using a U-tube viscometer or a rotational viscometer, such as a commercially available VISCOEASY rotational viscometer. Ethanol may used as a calibrating medium in the relevant measurement equipment, if necessary.

The second fluid medium preferably has a surface tension of 20 mNm$^{-1}$ or less, optionally 18 mNm$^{-1}$ or less, optionally 15 mNm$^{-1}$ or less, optionally 12 mNm$^{-1}$ or less. The surface tension of the second fluid medium is measured at standard temperature (25° C.) and pressure (101.325 kPa). Surface tension can be measured according to a standard method known to those skilled in the art, for example by using a tensiometer, e.g. a commercially available Kruss Tensiometer. Ethanol may used as a calibrating medium in the relevant measurement equipment, if necessary.

The conductivity of the second fluid medium is preferably 1×10$^{-8}$ Sm$^{-1}$ or less, optionally 1×10$^{-9}$ Sm$^{-1}$ or less, optionally 1×10$^{-10}$ Sm$^{-1}$ or less, optionally 1×10$^{-11}$ Sm$^{-1}$ or less. The conductivity of the second fluid medium is measured at standard temperature (25° C.) and pressure (101.325 kPa). Conductivity can be measured according to a standard method known to those skilled in the art, for example by using a conductivity probe, such as the commercially available HI-8733 conductivity probe, available from Sigma-Aldrich. Ethanol may used as a calibrating medium in the relevant measurement equipment, if necessary.

Preferably, the first and second fluid mediums are immiscible. Optionally the volatile liquid has a solubility in the liquid of the first fluid medium of 100 ppm or less, optionally 50 ppm or less, optionally 20 ppm or less, measured at standard temperature (25° C.) and pressure (101.325 kPa). In an embodiment, the first fluid medium comprises a non-halogenated organic solvent and the second fluid medium comprises a perhalocarbon and/or a halogenated hydrocarbon. In an embodiment, the first fluid medium comprises a non-halogenated organic solvent and the second fluid medium comprises a perfluorocarbon and/or a halogenated hydrocarbon having one or more fluorines on each molecule. The non-halogenated organic solvent may be selected from, but is not limited to, an aprotic solvent and a protic solvent. The non-halogenated organic solvent may be selected from ethanol, acetone, ethyl acetate, acetates, alcohol, ether, aliphatic, aromatic hydrocarbons, chlorinated hydrocarbons, ketones and chloroform. In an embodiment, the first fluid medium comprises a non-halogenated organic solvent and a polymer, and optionally the second fluid medium comprises a perfluorocarbon and/or a halogenated hydrocarbon.

One or more of the fluid mediums passed down the channels may comprise one or more pharmaceutically acceptable substances. Optionally all of the fluid mediums passed down the channels are pharmaceutically acceptable substances. The pharmaceutically acceptable substances may be carrier substances, suitable for acting as carriers for one or more agents selected from diagnostic and therapeutic agents. The carrier species may be an organic substance, optionally a polymeric substance. The carrier species is preferably a biocompatible carrier species. The carrier species may be selected from poly(lactic-co-glycolic acid) (PLGA), polycaprolactone (PCL), polymethylsilsesquioxane (PMSQ), perfluorohexane (PFH), perfluoropentane (PFP), polyurethane, starch, albumin, polyethylene oxide (PEO), glycerol and oil, such as olive oil.

The one or more fluid mediums, preferably the first fluid medium, may comprise a liquid having a pharmaceutically acceptable substance, e.g. the carrier substance, therapeutic agent and/or diagnostic agent as described herein, dispersed therein, e.g. dissolved therein or suspended therein. The liquid may comprise a polar or non-polar solvent. The liquid may comprise a protic or non-protic solvent. The liquid in the fluid medium may, for example, be as described above.

The rate of passing the fluid mediums through the device may be any suitable rate. The rates may be varied according to the nature of the fluid medium, and the desired type of layered bodies to be formed. The rate of passing the fluid mediums through the device may be, for each fluid medium being passed through each channel, from 1 µl/min to 2000 µl/min, optionally from 50 to 1000 µl/min, optionally from 100 to 800 µl/min.

Figure 1:
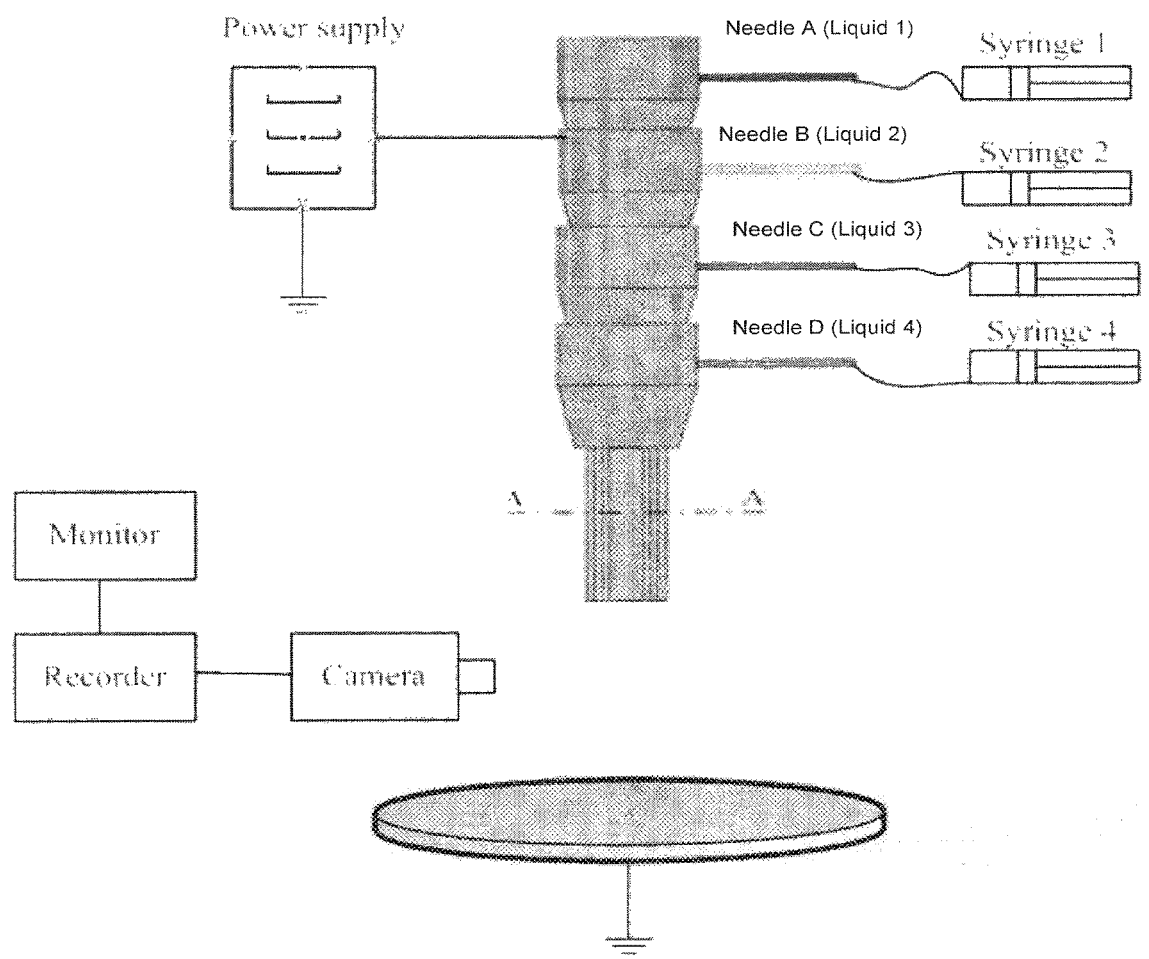
FIG. 1 shows an embodiment of the device of the present invention, the embodiment comprising a four-needle electrohydrodynamic system.

FIGS. 1, 2 and 3 shows an embodiment of the electrohydrodynamic device of the present invention. The device comprises four concentrically arranged, spaced apart hollow needles A, B, C and D, the needles together defining a core channel W, two intermediate concentrically disposed tubular channels X and Y, and an outer concentrically disposed tubular channel Z; and a means for applying a voltage to the needles.

As shown in FIG. 1, a syringe pump is fluidly connected to one end of each channel. The inner surface of the innermost needle A defines the core channel W. The core channel W is fluidly connected to syringe 1, which may be via any suitable conduit such as a tube, preferably a tube comprising silicone.

The outwardly disposed adjacent needle to the core needle is intermediate needle B. An intermediate concentrically disposed tubular channel X is defined by the outer surface of innermost needle A and inner surface of needle B. Tubular channel X is fluidly connected to syringe 2, which may be via any suitable conduit such as a tube, preferably a tube comprising silicone.

The outwardly disposed adjacent needle to intermediate needle B is intermediate needle C. An intermediate concentrically disposed tubular channel Y is defined by the outer surface of needle B and inner surface of needle C. Tubular channel Y is fluidly connected to syringe 3, which may be via any suitable conduit such as a tube, preferably a tube comprising silicone.

The outwardly disposed adjacent needle to intermediate needle C is outermost needle D. An outer concentrically disposed tubular channel Z is defined by the outer surface of innermost needle C and inner surface of needle D. Tubular channel Z is fluidly connected to syringe 4, which may be via any suitable conduit such as a tube, preferably a tube comprising silicone.

As shown in FIGS. 1, 2 and 3, all needles have a free end through which the fluid mediums being passed through the needles can exit. The fluid mediums exiting the needles will together be termed a fluid composition from hereon. At the end of the needles distal to the free end, each of needles A, B and C is in flush connection with the adjacent outwardly disposed needle.

Figure 2A:
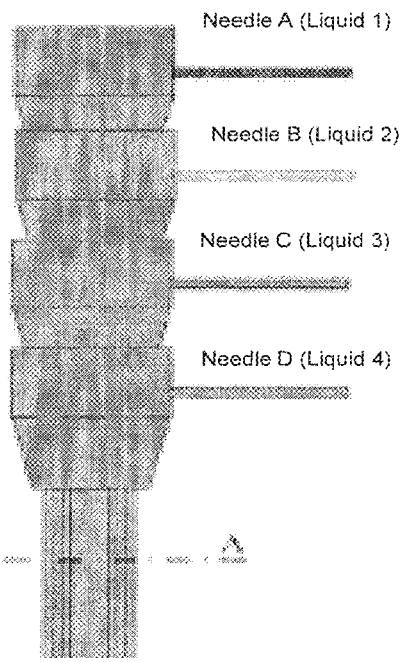
FIGS. 2A and 2B shows the four-needle electrohydrodynamic system of FIG. 1 in more detail, the use of which is described in the detailed description and Examples below.
Figure 2B:
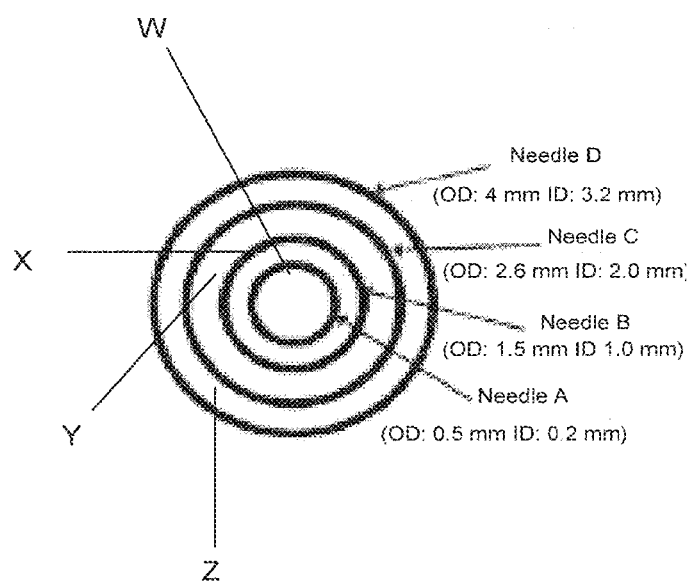

FIG. 2B shows a cross-sectional view of the needles and the channels they define along the line A-A of FIG. 2A. FIG. 2B shows the dimensions of a particular embodiment of the needles, as used in the Examples below. These dimensions can be varied and may be otherwise as described herein, depending on the desired size of the particles or threads that the skilled person wishes to produce with the device. In FIG. 2B, ID and OD represent, respectively, inner diameter and outer diameter.

In use, the needles may be orientated so that the axis of the needles is substantially vertical.

As shown in FIG. 1, a collection means is provided for collecting the layered body or bodies formed from the fluid composition after exiting the needles. The collection means is earthed. The collection means is disposed below the needles. The collection means may be in any suitable form, for example a plate or a receptacle.

Figures 3A, 3B:
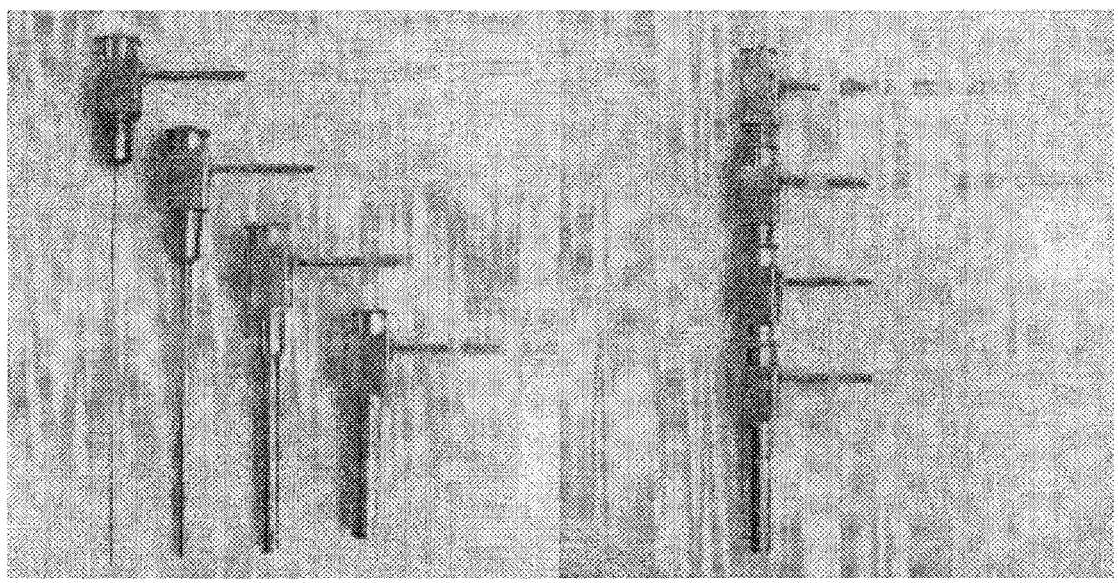
FIGS. 3A and 3B shows photographs of the needles used in the electrohydrodynamic system of FIGS. 1 and 2, with FIG. 3A showing the separate needles, and FIG. 3B showing the needles assembled.

FIGS. 3A and 3B show photographs of the needles used in the electrohydrodynamic system of FIGS. 1 and 2, with FIG. 3A showing the separate needles, and FIG. 3B showing the needles assembled. In FIG. 3A, the left hand needle is needle A, with needles B, C and D shown in order to the right.

In use, syringe 1 can provide a liquid 1 to channel W, preferably a second fluid medium as described herein. In use, syringe 2 can provide a liquid 2 to channel X, preferably a first fluid medium as described herein. In use, syringe 3 can provide a liquid 3 to channel Y, preferably a second fluid medium as described herein. In use, syringe 4 can provide a liquid 4 to channel Z, preferably a first fluid medium as described herein. Each of the syringes preferably supplies a fluid medium, e.g. the first or second fluid medium as described herein, at a suitable rate, e.g. a rate of from 1 µl/min to 2000 µl/min, to the channel to which it is fluidly connected. The rate of supply of the fluid medium for each channel may be the same as or different to one or more of the other channels, e.g. the adjacent channel disposed outwardly or inwardly.

Figures 4A, 4B:
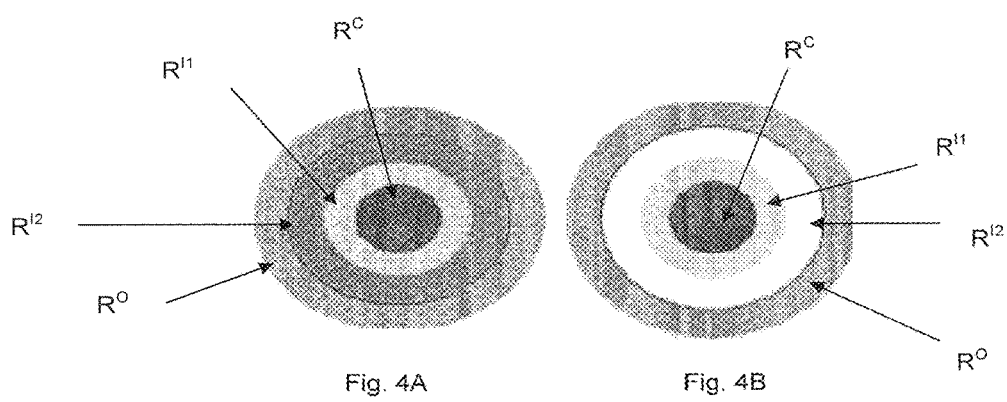
FIGS. 4A to 4D show schematic cross-sectional views of embodiments of the layered bodies of the present invention.
Figures 4C, 4D:
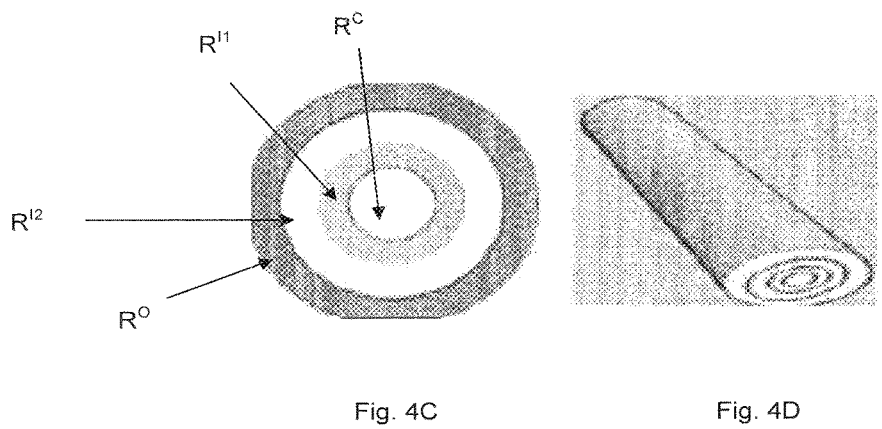

FIGS. 4A to 4D show embodiments of the layered bodies of the present invention. In FIGS. 4A to 4C, the layered bodies are in the form of a capsule. In FIG. 4C, the layered body is in the form of a thread.

The layered body in FIG. 4A is in the form of a capsule and comprises: a core region $R^C$; two intermediate layers, $R^{I1}$ and $R^{I2}$, disposed around, e.g. concentrically around, the core region; an outer layer $R^O$ disposed around, e.g. concentrically around, the two intermediate layers. The diameter of the capsule is typically 100 µm or less. In the embodiment shown in FIG. 4A, the core region is substantially spherical. The intermediate layers and the outer layer are in the form of approximate spheres. In the embodiment shown in FIG. 4A, the core region $R^C$ is in the form an approximately spherical particle having a coating of intermediate layer $R^{I1}$ surrounding the particle. The core region, the intermediate layers $R^{I1}$ and $R^{I2}$, and the outer layer $R^O$ all comprise liquid or solid materials. This is an embodiment of the second aspect of the invention. The body shown in FIG. 4A may be produced using the device shown in FIGS. 1 to 3B. In the process, the first fluid medium is passed down each of the four channels and an appropriate voltage applied to the needles, such that, when the fluid mediums exit the needles, they form a jet that breaks up into droplets, the droplets being in the form of the capsule shown in FIG. 4A. The droplets are collected on or in the earthed collecting means.

Figure 8:
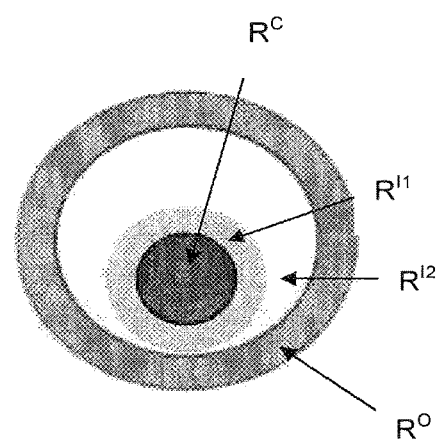
FIG. 8 shows the layered body of FIG. 4B, with the core region $R^C$ and surrounding intermediate layer $R^{I1}$ having shifted due to gravity within the gas-containing layer $R^{I2}$, such that it is in contact with the outer layer $R^O$.

The layered body in FIG. 4B is in the form of a capsule and comprises: a core region $R^C$; two intermediate layers, $R^{I1}$ and $R^{I2}$ disposed around, e.g. concentrically around, the core region; an outer layer $R^O$ disposed around, e.g. concentrically around, the two intermediate layers. The diameter of the capsule is typically 100 µm or less. In the embodiment shown in FIG. 4B, the core region $R^C$ is in the form an approximately spherical particle having a coating of intermediate layer $R^{I1}$ surrounding the particle. The core region, the intermediate layers $R^{I1}$, and the outer layer $R^O$ all comprise liquid or solid materials. The intermediate layer $R^{I2}$ is a substantially hollow region comprising a gas, for example air. This is an embodiment of the first and second aspects of the invention. The body shown in FIG. 4B may be produced using the device shown in FIGS. 1 to 3B. In the process, the first fluid medium as described herein is passed down each of the channels W, X and Z, a second fluid medium as described herein, is passed down channel Y and an appropriate voltage applied to the needles, such that, when the fluid mediums exit the needles, they form a jet that breaks up into droplets, the droplets being in the form of the capsule shown in FIG. 4B. The droplets are collected on or in the earthed collecting means. The core and intermediate layers may alter positions to a small extent, such that the core region $R^C$ and surrounding intermediate layer $R^{I1}$ shift, e.g. due to gravity, within the gas-containing layer $RR^{I2}$, such that the layer intermediate layer $R^{I1}$ is in contact with the outer layer $R^O$. This is shown in FIG. 8. The layered body of FIG. 8 is nevertheless encompassed by the first and second aspects of the invention.

Figure 9:
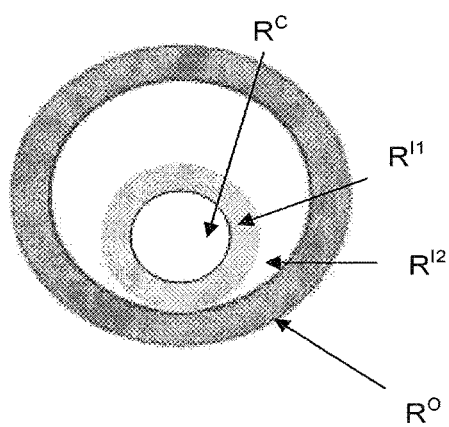
FIG. 9 shows the layered body of 4C, with the with the core region $R^C$ and surrounding intermediate layer $R^{I1}$ having shifted due to gravity within the gas-containing layer $R^{I2}$, such that it is in contact with the outer layer $R^O$.

The layered body in FIG. 4C is in the form of a capsule and comprises: a core region $R^C$; two intermediate layers, $R^{I1}$ and $R^{I2}$ disposed around, e.g. concentrically around, the core region; an outer layer $R^O$ disposed around, e.g. concentrically around, the two intermediate layers. The diameter of the capsule is typically 100 µm or less. In the embodiment shown in FIG. 4C, the core region is substantially spherical. The intermediate layers and the outer layer are in the form of approximate spheres. The intermediate layer $RR^{I1}$, and the outer layer $R^O$ all comprise liquid or solid materials. The core region $R^O$ and the intermediate layer $R^{I2}$ are substantially hollow regions comprising a gas, for example air. This is an embodiment of the first and second aspects of the invention. The body shown in FIG. 4C may be produced using the device shown in FIGS. 1 to 3B. In the process, the first fluid medium as described herein is passed down each of the channels X and Z, the second fluid medium as described herein is passed down channels W and Y and an appropriate voltage applied to the needles, such that, when the fluid mediums exit the needles, they form a jet that breaks up into droplets, the droplets being in the form of the capsule shown in FIG. 4C. The droplets are collected on or in the earthed collecting means. The core and intermediate layers may alter positions to a small extent, such that the core region $R^C$ and surrounding intermediate layer $R^{I1}$ shift, e.g. due to gravity, within the gas-containing layer $R^{I2}$, such that the layer intermediate layer $RR^{I1}$ is in contact with the outer layer $R^O$. This is shown in FIG. 9. The layered body of FIG. 9 is nevertheless encompassed by the first and second aspects of the invention.

The layered body in FIG. 4D is in the form of a thread and comprises: a core region; two intermediate layers, disposed around, e.g. concentrically around, the core region; an outer layer disposed around, e.g. concentrically around, the two intermediate layers. The core is elongated and has an axis, and the two intermediate layers and the outer layer are disposed around, e.g. concentrically around, the axis. As can be seen in FIG. 4D, the core forms a substantially cylindrical core. The two intermediate layers and the outer layer are also in the form of approximate cylinders. The content of the core region, intermediate layers and the outer layer of the thread may be as described for the particles shown in FIGS. 4A, 4B and 4C. Threads according to FIG. 4D may be produced using the device shown in FIGS. 1 to 3B. It has been found that the formation of a threads can be promoted by dissolving or suspending a suitable material in a fluid medium in an appropriate concentration, this fluid medium being passed down one of the channels of the device. For example, threads have been found to be promoted if at least one of the fluid mediums being passed down the channels contains a polymeric material in an amount of 60% or more by weight. For example, threads have been found to be promoted if at least one of the fluid mediums being passed down the channels contains a non-polymeric material in an amount of 50% or more by weight.

The present invention further provides a composition comprising a plurality of bodies of the first aspect and/or a plurality of bodies of the second aspect. The plurality of bodies may contain a collection of bodies all according to the first aspect or the second aspect, but nevertheless having differing characteristics, for example being of different diameters and/or having different compositions.

The present invention further provides a plurality of bodies obtainable by a method according to the fourth aspect and/or a method according to the fifth aspect. The plurality of bodies may contain a collection of bodies all obtainable by a method according to the fourth aspect and/or a method according to the fifth aspect, but nevertheless having differing characteristics, for example being of different diameters and/or having different compositions.

The present invention will now be described in the following non-limiting Examples.

EXAMPLES

The following Examples illustrate a process of producing layered bodies according to the present invention.

The four-needle electrohydrodynamic device used in the Examples was as shown in FIGS. 1 to 3B, and as described above. The dimensions of the needles was as shown in FIG. 2B, and the connectivity of each needle and channel as shown in FIGS. 1 and 2A. The flow rates of fluid mediums supplied to the channels were controlled by four high-precision programmable syringe pumps (available from Harvard PHD 4400, Apparatus, Edenbridge, UK), labelled Syringe 1, 2, 3 and 4 in FIG. 1.

An electric field between the needles and a ring-shaped ground electrode (not shown in Figures, external and internal diameters of 20 and 15 mm, respectively) was controlled by a high-voltage generator (obtained from Glassman Europe Limited, Bramley, UK).

The distance from the exit of the outer needle to the ground electrode (the working distance) was fixed at 12 mm in all the experiments. The flow of the liquids under the influence of the electric field was visualized using a video camera (LEICA S6D JVC-colour).

Properties of the fluid mediums used in the Examples are given below in Table 1.

TABLE 1

| Fluid Medium | Density $kgm^{-3}$ | Viscosity $mPa\,s$ | Surface tension $mNm^{-1}$ | Electrical conductivity $Sm^{-1}$ |
| --- | --- | --- | --- | --- |
| Perfluorohexane | 1710 | 1.1 | 12 | $<1 \times 10^{-11}$ |
| Ethanol containing 18 wt % of PMSQ | 805 | 1.8 | 23 | $9 \times 10^{-5}$ |

The perfluorohexane represents an example of a second fluid medium as described herein. The ethanol containing 18 wt % of PMSQ represents an example of a first fluid medium as described herein.

For the measurement of density, viscosity, surface tension and electrical conductivity, ethanol was used as the calibrating medium in the relevant measurement equipment used. The density of each fluid medium was measured using a standard 25 ml density bottle. The surface tension values of each fluid medium were measured using a Kruss Tensiometer. Viscosity values were determined using a U-tube viscometer and a VISCOEASY rotational viscometer. Electrical conductivity values were estimated using a HI-8733 conductivity probe.

Example 1

In this example, the syringe 1 of the device was loaded with the compound PFH (perfluorohexane), obtained from F2 Chemicals Ltd. This was supplied to channel W at a rate of 300 µl per minute.

Syringe 2 was loaded with ethanol containing 18 wt % of the polymer polymethylsilsesquioxane (PMSQ), obtained from Wacker Chemie AG, GmbH. This was supplied to channel X at a rate of 600 µl per minute.

Syringe 3 was loaded with PFH. This was supplied to channel Y at a rate of 300 µl per minute.

Syringe 4 was loaded with ethanol containing 18 wt % of the polymer polymethylsilsesquioxane (PMSQ). This was supplied to channel Z at a rate of 600 µl per minute.

The voltage applied to the needles was 20 kV.

Figure 5:
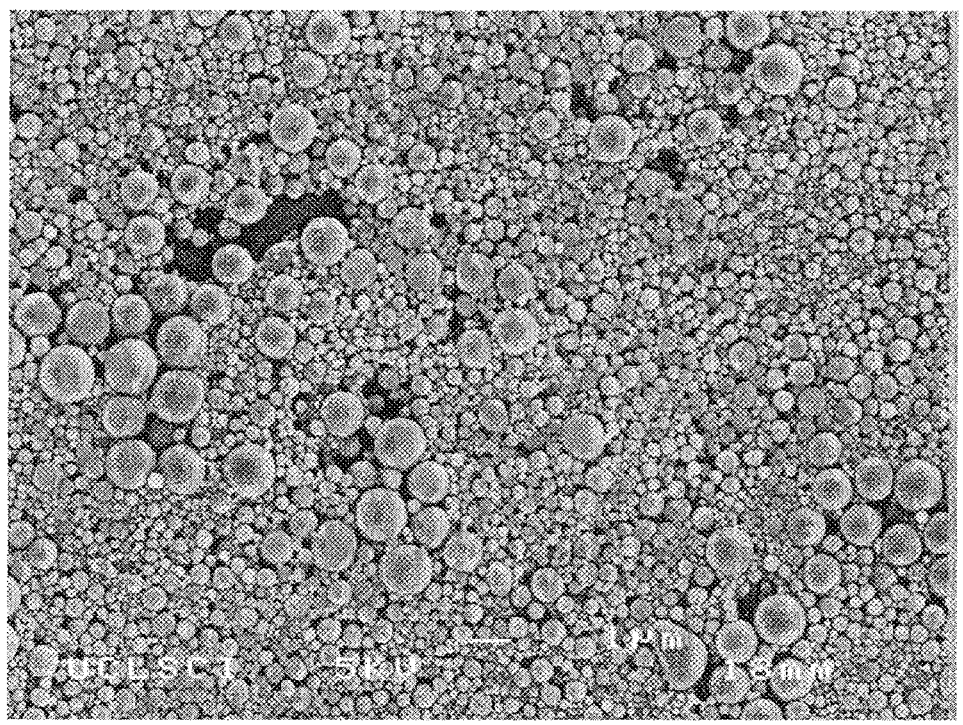
FIG. 5 shows an embodiment of a composition comprising a plurality of layered bodies of the present invention, in particulate or capsule form, obtained as described in the Examples below.

A jet was found to form, which broke up to form droplets or capsules, i.e. an embodiment of the layered bodies of the invention. It is considered that the cross section of the capsules may be represented schematically by FIG. 4C. A collection of the capsules is shown in FIG. 5. Scanning electron microscopy (SEM, JEOL JSM-6301F field emission scanning electron microscope) was used to obtain this image and study the size of the as-formed products. 200 microspheres were analyzed from the SEM images to calculate the mean diameter of the capsules, this mean being the number mean. The mean diameter of the capsules was found to be 510 nm. The maximum diameter of the capsules was found to be 1350 nm. The minimum diameter of the capsules was found to be 35 nm.

Example 2

In this example, the syringe 1 of the device was loaded with the compound PFH (perfluorohexane), obtained from F2 Chemicals Ltd. This was supplied to channel W at a rate of 300 µl per minute.

Syringe 2 was loaded with ethanol containing 18 wt % of the polymer polymethylsilsesquioxane (PMSQ), obtained from Wacker Chemie AG, GmbH. This was supplied to channel X at a rate of 300 µl per minute.

Syringe 3 was loaded with PFH. This was supplied to channel Y at a rate of 300 µl per minute.

Syringe 4 was loaded with ethanol containing 18 wt % of the polymer polymethylsilsesquioxane (PMSQ). This was supplied to channel Z at a rate of 300 µl per minute.

The voltage applied to the needles was 20 kV.

Figure 6:
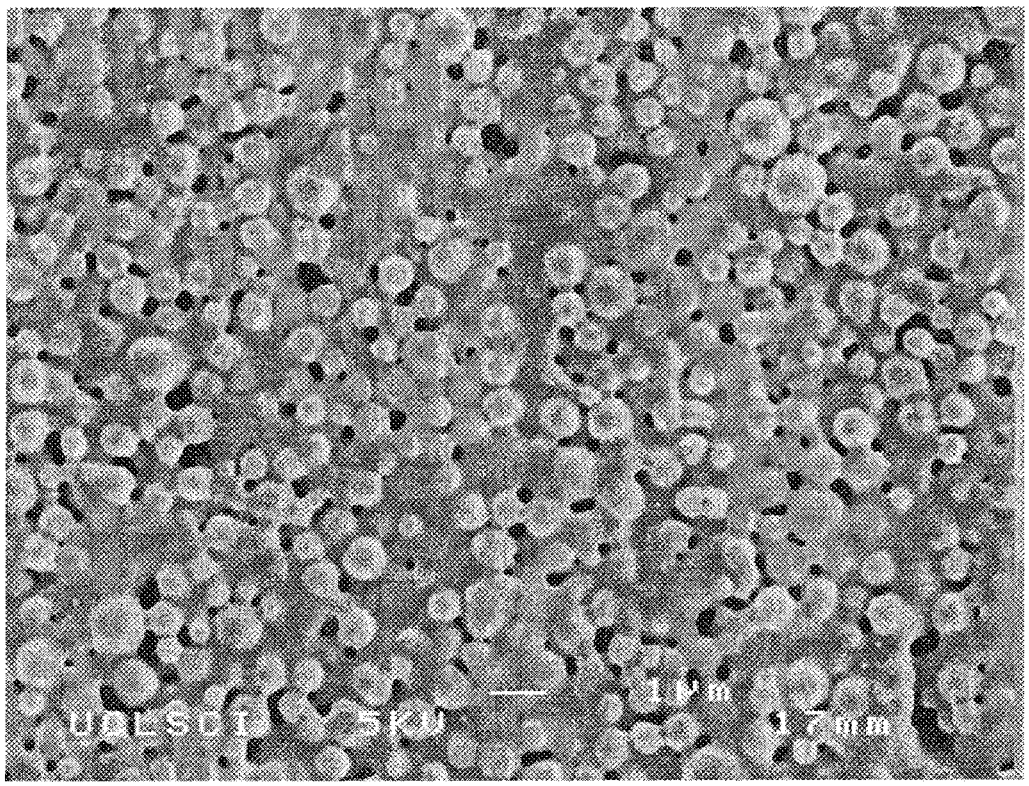
FIG. 6 shows an embodiment of a composition comprising a plurality of layered bodies of the present invention, in particulate or capsule form, obtained as described in the Examples below.

A jet was found to form, which broke up to form droplets or capsules, i.e. an embodiment of the layered bodies according to the invention. It is considered that the cross section of the capsules may be represented schematically by FIG. 4C. A collection of the capsules is shown in FIG. 6. Scanning electron microscopy (SEM, JEOL JSM-6301F field emission scanning electron microscope) was used to obtain this image and study the size of the as-formed products. 200 microspheres were analyzed from the SEM images to calculate the mean diameter of the capsules, this mean being the number mean. The mean diameter of the capsules was found to be 590 nm. The maximum diameter of the capsules was found to be 1062 nm. The maximum diameter of the capsules was found to be 233 nm.

What is claimed is:

1. A layered body comprising:
a core region;
at least one intermediate layer; and
an outer layer, wherein:
(1) the at least one intermediate layer and the outer layer are disposed concentrically around the core region, such that the at least one intermediate layer surrounds the core region and the outer layer surrounds the at least one intermediate layer; and
(2) the layered body has a diameter of 100 μm or less as measured by scanning electron microscopy; and
wherein either:
(i) each of the core region and the outer layer is solid and comprises a biocompatible polymer and the at least one intermediate layer disposed between the core region and the outer layer comprises a halogenated hydrocarbon gas; or
(ii) the core region comprises a gas, and the at least one intermediate layer comprises a first intermediate layer and a second intermediate layer, wherein the first intermediate layer is solid, surrounds the core region, and comprises a biocompatible polymer, and the second intermediate layer comprises a halogenated hydrocarbon gas disposed between the first intermediate layer and the outer layer, and the outer layer is solid and comprises a biocompatible polymer;
wherein the layered body is spherical and formed in an electrohydrodynamic process;
wherein the biocompatible polymer is selected from the group consisting of sodium polystyrene sulfonate, polyethers, polyethylene imine, polylactic acid, polycaprolactone, polyglycolic acid, and poly(lactic-co-glycolic acid); and
wherein the halogenated hydrocarbon gas of the intermediate layer in (i) or (ii) comprises a halogenated hydrocarbon compound having 10 carbons or less.

2. The layered body according to claim 1, wherein the layered body has the structure of (ii) comprising the first intermediate layer surrounding the core region, and the second intermediate layer disposed between the first intermediate layer and the outer layer.

3. The layered body according to claim 1, wherein the core region comprises a first active agent, and the outer layer comprises a second active agent different from the first active agent.

4. The layered body according to claim 1, wherein at least one of the core region, the at least one intermediate layer, or the outer layer comprises a therapeutic agent or a diagnostic agent.

5. A composition comprising a plurality of layered bodies according to claim 1.

6. The layered body according to claim 1, wherein the biocompatible polymer comprises a polyether selected from the group consisting of polyethylene oxides, polyethylene glycols, and cellulose ether polymers.

7. The layered body according to claim 3, wherein the layered body is in the form of a time-release capsule.

8. The layered body according to claim 3, wherein at least one of the first active agent or the second active agent is an antibiotic.

9. A layered body comprising:
a core region that comprises a biocompatible polymer selected from the group consisting of polylactic acid, polycaprolactone, polyglycolic acid, poly(lactic-co-glycolic acid), polymethylsilsesquioxane, and cellulose ether polymers;
an intermediate layer that comprises a gas; and
an outer layer that is solid, wherein the intermediate layer and the outer layer are disposed concentrically around the core region, such that the intermediate layer surrounds the core region and the outer layer surrounds the intermediate layer;
wherein the gas of the intermediate layer is air;
wherein the layered body is spherical and has a diameter of 100 μm or less as measured by scanning electron microscopy, and
wherein the layered body is formed in an electrohydrodynamic process using a voltage of 15 kV to 25 kV.

10. The layered body according to claim 9, wherein the core region comprises an active agent, and the outer layer comprises a cellulose ether polymer.

11. The layered body according to claim 9, wherein the core region or the outer layer comprises a peptide, DNA, or RNA.

12. A composition comprising the layered body according to claim 9, wherein the composition is a pharmaceutical composition.

13. A composition comprising a plurality of layered bodies according to claim 1 and at least one additional layered body comprising:
a core region comprising a biocompatible polymer selected from the group consisting of sodium polystyrene sulfonate, polyethers, polyethylene imine, polylactic acid, polycaprolactone, polyglycolic acid, and poly(lactic-co-glycolic acid);
an intermediate layer of air or a halogenated hydrocarbon gas comprising a halogenated hydrocarbon compound having 10 carbons or less; and
an outer layer comprising a biocompatible polymer that is the same or different from the biocompatible polymer of the core region, the biocompatible polymer of the outer layer being selected from the group consisting of sodium polystyrene sulfonate, polyethers, polyethylene imine, polylactic acid, polycaprolactone, polyglycolic acid, and poly(lactic-co-glycolic acid);
wherein the at least one additional layered body is spherical and has a diameter of 100 μm or less as measured by scanning electron microscopy.

14. The composition of claim 13, wherein each layered body of the plurality of layered bodies comprises a first active agent, and the at least one additional layered body comprises a second active agent different from the first active agent.

15. A layered body comprising:
a core region comprising a first gas selected from the group consisting of oxygen, nitrogen, air, and a halogenated hydrocarbon gas comprising a halogenated hydrocarbon compound having 10 carbons or less;
an outer layer comprising a polymer selected from the group consisting of sodium polystyrene sulfonate, polyethers, polyethylene imine, polylactic acid, polycaprolactone, polyglycolic acid, and poly(lactic-co-glycolic acid); and
at least two intermediate layers between the core region and the outer layer, the at least two intermediate layers comprising:

a first intermediate layer adjacent to the core region, the first intermediate layer comprising a polymer that is the same or different than the polymer of the outer layer, the polymer of the first intermediate layer being selected from the group consisting of sodium polystyrene sulfonate, polyethers, polyethylene imine, polylactic acid, polycaprolactone, polyglycolic acid, and poly(lactic-co-glycolic acid); and a second intermediate layer between the first intermediate layer and the outer layer, the second intermediate layer comprising a second gas different from the first gas, the second gas being selected from the group consisting of oxygen, nitrogen, air, and a halogenated hydrocarbon gas comprising a halogenated hydrocarbon compound having 10 carbons or less;

wherein the layered body is spherical and has a diameter of 100 μm or less as measured by scanning electron microscopy.

16. The layered body according to claim 15, wherein the first gas or the second gas is air.

* * * * *